United States Patent [19]

Benicewicz et al.

[11] Patent Number: 5,315,011

[45] Date of Patent: May 24, 1994

[54] POLYAMIDE THERMOSETS

[75] Inventors: Brian C. Benicewicz; Andrea E. Hoyt, both of Los Alamos, N. Mex.

[73] Assignee: The United States of America as represented by the United States Department of Energy, Washington, D.C.

[21] Appl. No.: 941,815

[22] Filed: Sep. 8, 1992

Related U.S. Application Data

[60] Division of Ser. No. 711,721, Jun. 7, 1991, Pat. No. 5,198,551, which is a continuation of Ser. No. 506,742, Apr. 10, 1990, abandoned.

[51] Int. Cl.$^5$ .......................................... C07D 403/10
[52] U.S. Cl. .................................. 548/521; 548/435; 548/548; 564/155
[58] Field of Search .................. 548/548, 435, 521; 564/155

[56] References Cited

U.S. PATENT DOCUMENTS 4,269,966  5/1981  Steuzenberger ............... 548/521
5,132,431  7/1992  Fuchs et al. ..................... 548/435

Primary Examiner—David B. Springer
Attorney, Agent, or Firm—Bruce H. Cottrell; Paul D. Gaetjens; William R. Moser

[57] ABSTRACT

The present invention provides (1) curable polyamide monomers represented by the formula: $R^1$—$A^1$—$B^1$—$A^2$—$B^2$—$A^3$—$R^2$ where $R^1$ and $R^2$ are radicals selected from the group consisting of maleimide, substituted maleimide, nadimide, substituted nadimide, ethynyl, and $(C(R^3)_2)_2$ where $R_3$ is hydrogen with the proviso that the two carbon atoms of $(C(R^3)_2)_2$ are bound on the aromatic ring of $A^1$ or $A^3$ to adjacent carbon atoms, $A^1$ and $A^3$ are 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and $B^1$ and $B^2$ are selected from the group consisting of —C(O)—N(H)— and —N(H)—C(O)—, (2) thermoset polyamide compositions comprised of cured segments derived from monomers represented by the formula: $R^1$—$A^1$—$B^1$—$A^2$—$B^2$—$A^3$—$R^2$ as described above, and curable blends of at least two of the polyamide monomers and (4) processes of preparing the curable polyamide monomers.

6 Claims, 2 Drawing Sheets

POLYAMIDE THERMOSETS

FIELD OF THE INVENTION

The present invention relates to the field of curable polyamide monomers, curable liquid crystal polyamide monomers and to thermoset polyamide compositions prepared therefrom. This invention is the result of a contract with the Department of Energy (Contract No. W-7405-ENG-36).

This is a division of application Ser. No. 711,721 filed Jun. 7, 1991, now U.S. Pat. No. 5,198,551, which is a continuation of application Ser. No. 506,742 filed Apr. 10, 1990, now abandoned.

BACKGROUND OF THE INVENTION

Liquid crystal polymers are recognized as having great potential for the development of new materials with exceptional physical and mechanical properties. In general, liquid crystal polymers consist of polymer chains containing anisotropic structural units (mesogenic groups) which may be incorporated into the polymer backbone, as pendent groups, or both. The mesogenic groups may be rod-like or disc-like in nature. Fibers, films, and molded plastics processed from the liquid crystalline state have shown outstanding properties.

Another desirable characteristic of such liquid crystalline polymers would be that they be thermosetting. Liquid crystal thermosetting polymers are known, e.g., the acrylic-terminated thermoset resins and precursors disclosed by Conciatori et al. in U.S. Pat. Nos. 4,440,945, 4,452,993, and 4,514,553, the epoxy-terminated thermoset resins and precursors disclosed by Muller et al. in U.S. Pat. No. 4,764,581, and the various difunctionally terminated materials disclosed by Dhein et al. in U.S. Pat. No. 4,762,901.

Another type of thermosetting resins utilizing end groups such as maleimide, nadimide and methyl nadimide are described in various patents such as U.S. Pat. Nos. 4,225,497, 4,550,177, 4,739,030, 4,661,604, 4,684,714, 4,851,495, and 4,851,501.

Accordingly, it is an object of this invention to provide curable polyamide materials including curable liquid crystalline polyamide materials.

Another object of this invention is to provide a process of preparing curable polyamide materials including curable liquid crystal polyamide monomers.

Yet another object of this invention is to provide curable blends of polyamide materials including curable liquid crystal polyamide materials.

It is a further object of this invention to provide thermoset polyamide compositions including thermoset liquid crystal polyamide compositions.

It is a still further object of this invention to provide thermoset polyamide compositions having a high heat resistance including thermoset liquid crystalline polyamide compositions having a high heat resistance.

SUMMARY OF THE INVENTION

To achieve the foregoing and other objects, and in accordance with the purposes of the present invention, as embodied and broadly described herein, the present invention provides a curable polyamide monomer represented by the formula: $R^1-A^1-B^1A^2-B^2-A^3-R^2$ where $R^1$ and $R^2$ are radicals selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ or $A^3$ to adjacent carbon atoms, $A^1$ and $A^3$ are 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and $B^1$ and $B^2$ are selected from the group consisting of $-C(O)-N(H)-$, or $-N(H)-C(O)-$. Preferably, $R^1$ and $R^2$ are radicals selected from the group consisting of maleimide, nadimide, methyl nadimide, and ethynyl.

The present invention further provides a thermoset polyamide composition comprised of cured segments derived from one or more monomer represented by the formula: $R^1-A^1-B^1A^2-B^2-A^3-R^2$ where $R^1$ and $R^2$ are radicals selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ or $A^3$ to adjacent carbon atoms, $A^1$ and $A^3$ are 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and $B^1$ and $B^2$ are selected from the group consisting of $-C(O)-N(H)-$, or $-N(H)-C(O)-$. Preferably, $R^1$ and $R^2$ are radicals selected from the group consisting of maleimide, nadimide, methyl nadimide, and ethynyl.

The present invention still further provides a process of preparing a curable polyamide monomer represented by the formula: $R^1-A^1-B^1A^2-B^2-A^3-R^2$ where $R^1$ and $R^2$ are radicals selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ or $A^3$ to adjacent carbon atoms, $A^1$ and $A^3$ are 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and $B^1$ and $B^2$ are selected from the group consisting of —C(O)—N(H)—, or —N(H)—C(O)—, said process comprising: reacting a difunctional compound represented by the formula $B^3$—$A^2$—$B^4$ wherein $B^3$ and $B^4$ are selected from the group consisting of —$NH^2$ or —$NH^2$.HCl, and $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, with an acid chloride represented by the formula: Cl—C(O)—$A^1$—$R^1$ wherein $A^1$ is 1,4-phenylene and the same containing one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and $R^1$ is a radical selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ or $A^3$ to adjacent carbon atoms. Preferably, $R^1$ and is a radical selected from the group consisting of maleimide, nadimide, methyl nadimide, and ethynyl.

DETAILED DESCRIPTION

The present invention is concerned with curable or thermosettable polyamide compounds or monomers including curable or thermosettable liquid crystalline polyamide compounds or monomers represented by the formula $R^1$—$A^1$—$B^1A^2$—$B^2$—$A^3$—$R^2$ where $R^1$ and $R^2$ are radicals selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ or $A^3$ to adjacent carbon atoms, $A^1$ and $A^3$ are 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and $B^1$ and $B^2$ are selected from the group consisting of —C(O)—N(H)—, or —N(H)—C(O)—. Where $R^1$ and $R^2$ are substituted maleimide or substituted nadimide, the substituents can include one or two groups selected from among lower alkyl, lower alkoxy, aryl, aryloxy, halogen, substituted alkyl, or substituted alkoxy upon the ring. Also, the bridging methylene group in nadimide may be replaced by groups such as oxo, thio, or sulfone. Preferably, $R^1$ and $R^2$ are radicals selected from the group consisting of maleimide, nadimide, methyl nadimide, and ethynyl.

Figure 1A:
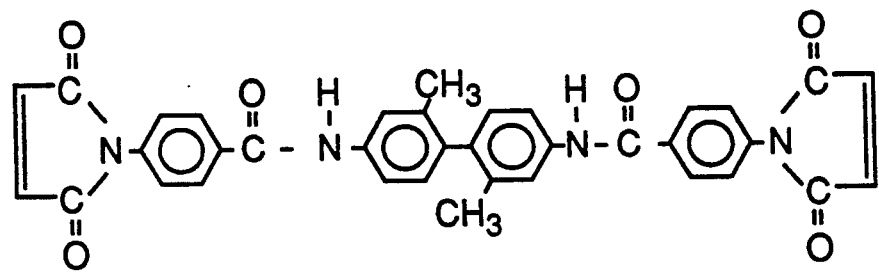
FIG. 1(a)-(g) depict, by structural formula polyamide monomers or compounds of the present invention.
Figure 1B:
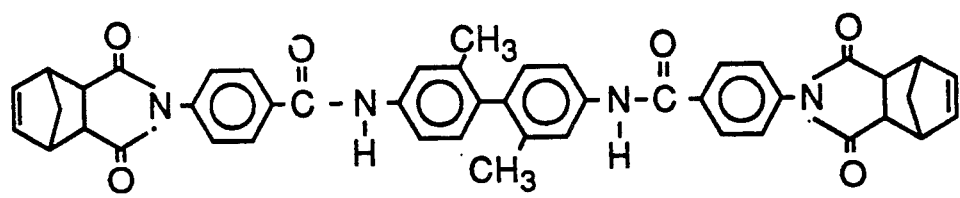
Figure 1C:
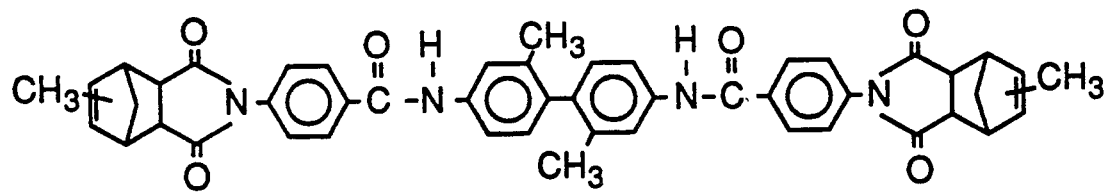
Figure 1D:
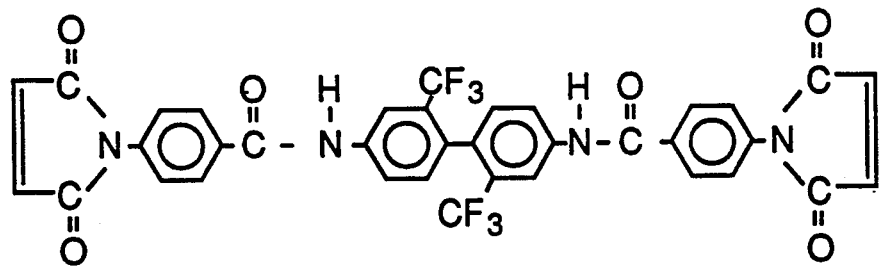
Figure 1E:
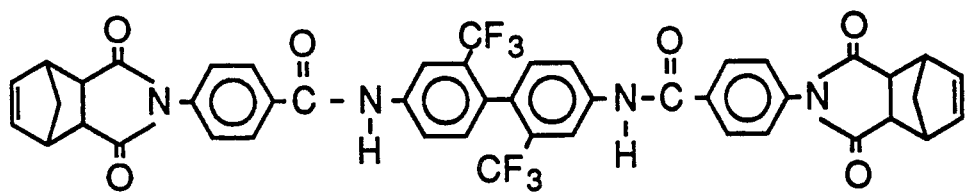
Figure 1F:
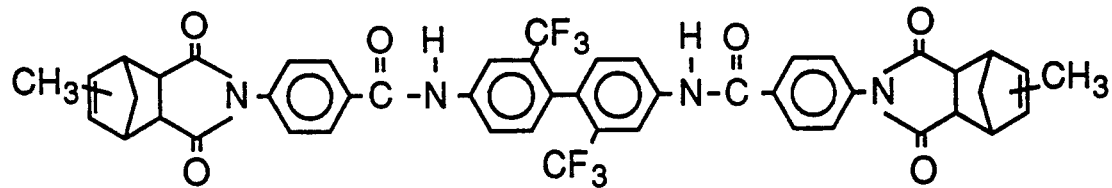
Figure 1G:
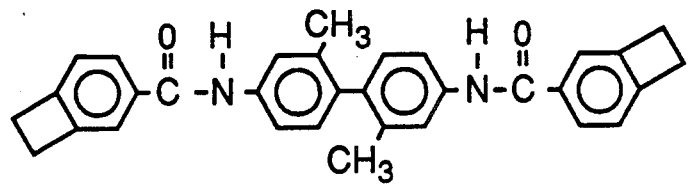

Throughout the present description, where $A^1$ or $A^3$ are bound to a $(C(R^3)_2)_2$ moiety, the combination of such can be referred to as a benzocyclobutene group. FIG. 1(g) illustrates, e.g., the 2,2'-dimethylbiphenyl benzocyclobutene amide monomer.

Such curable polyamide compounds or monomers can be prepared by a process including reacting a difunctional compound represented by the formula $B_3$—$A^2$—$B_4$ wherein $B_3$ and $B_4$ are selected from the group consisting of —$NH^2$ or —$NH^2$ and $A^2$ is selected from the group consisting of 1,4-phenylene, 4,4'-biphenyl, 2,6-naphthylene and the same where said groups contain one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, with an acid chloride represented by the formula Cl—C(O)—$A^{(1\ or\ 3)}$—$R^{(1\ or\ 2)}$ wherein $A^{(1\ or\ 3)}$ is selected from the group consisting of 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and either $R^{(1\ or\ 2)}$ is a radical selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ or $A^3$ to adjacent carbon atoms. Preferably, $R^1$ and $R^2$ are radicals selected from the group consisting of maleimide, nadimide, methyl nadimide, and ethynyl. In this process, i.e., the reaction of the diamine with the acid chloride containing the end-capped groups, the result is a polyamide compound or monomer wherein the carbonyl of $B^1$ and $B^2$ are adjacent to $A^1$ or $A^3$. To obtain the preferred products the diamine is reacted with the acid chloride in a ratio of diamine:acid chloride of 1:2. An acid scavenger such as triethylamine or the like can be added to the reaction mixture. In a similar manner, the reaction of a diacid chloride with an aminobenzene containing the end-capped groups may yield a polyamide compound or monomer wherein the carbonyl of $B^1$ and $B^2$ are adjacent to $A^2$.

The acid chlorides represented by the formula Cl—C(O)—$A^{(1\ or\ 3)}$—$R^{(1\ or\ 2)}$ wherein $A^{(1\ or\ 3)}$ is selected from the group consisting of 1,4-phenylene and the same where said group contains one or more substituents selected from the group consisting of halo, e.g., fluoro, chloro, bromo, or iodo, nitro, lower alkyl, e.g., methyl, ethyl, and propyl, lower alkoxy, e.g., methoxy, ethoxy, or propoxy, and fluoroalkyl or fluoroalkoxy, e.g., trifluoromethyl, pentafluoroethyl and the like, and either $R^{(1\ or\ 2)}$ is a radical selected from the group consisting of maleimide, substituted maleimide, nadimide, or substituted nadimide, can be prepared by reacting para-aminobenzoic acid with the respective anhydride to obtain the respective amic acid, cyclodehydrating the amic acid with a mixture of acetic anhydride and sodium acetate to obtain an intermediate product, and finally reacting the intermediate product with oxalyl chloride to obtain the acid chloride.

Curable blends of the polyamide compounds including blends with one or more liquid crystalline polyamide compounds are also provided by this invention. Such blends can allow the tailoring of properties such as melting points which may lower the processing temperature of these materials. For example, by blending two or more of the polyamide monomers the melting point of the blend can be depressed beneath that of the individual monomers. Where one or more of the polyamide monomers are liquid crystalline, the blend may retain the liquid crystallinity of the monomers. The polyamide monomers or compounds are represented by the formula $R^1-A^1-B^1A^2-B^2-A^3-R^2$ where $R^1$, $R^2$, $A^1$, $A^2$, $A^3$, $B^1$ and $B^2$ are as previously described.

The polyamide monomers can be polymerized by heat alone, or by the action of free radical initiators, or by the addition of aromatic polyamines as bridging agents, or by the presence of a catalytic amount of an alkali metal salt of a Bronsted acid. Preferably, with monomers including the end groups of ethynyl and benzocyclobutene, such monomers are polymerized by heat.

In addition to homopolymerization, the polyamide monomers can be polymerized with various vinyl monomers such as styrene, acrylonitrile, acrylates and methacrylates, or with other type maleimide capped compounds. Such copolymerizations can be initiated by free radical generating materials such as peroxides, azo compounds, etc. as well known to one skilled in the art of polymerization.

The end-capped compounds of the present invention can be used in forming prepregs or composites as is standard in the art. Crosslinking with the end-capped compounds generally can occur with heat alone upon heating the compounds to from about 230° C. to about 370° C., preferably from about 260° C. to about 340° C.

Prepregs of the end-capped compounds can be prepared by conventional techniques. While woven fabrics are the typical reinforcement, the fibers can be continuous or discontinuous, i.e., in chopped or whisker form, and may be ceramic, organic, glass, or carbon, i.e., graphite, as is desired for the particular application.

Composites can be formed by curing the end-capped compounds or prepregs in conventional vacuum bag techniques. The end-capped compounds may also be used as adhesives, varnishes, films, or coatings.

The present invention is more particularly described in the following examples which are intended as illustrative only, since numerous modifications and variations will be apparent to those skilled in the art.

EXAMPLE A

N-(para-carboxyphenyl)maleimide was prepared as follows. Maleic anhydride (45.2 grams (g)) was dissolved in from 300–400 milliliters (ml) of acetone. To this solution, an equimolar amount of para-aminobenzoic acid (63.2 g) was added with rapid stirring. The reaction mixture solidified within a few seconds. Excess solvent was removed by evaporation to yield the amic acid intermediate which was then dried overnight at 65° C. under vacuum.

The dried intermediate material was then dissolved in 200 ml of dimethyl formamide and heated to 45° C. Acetic anhydride (72 ml) and anhydrous sodium acetate (3.6 g) were then added with stirring. The reaction was allowed to proceed at 45° C. for two hours after which the mixture was poured into one liter of water slightly acidified by addition of 10 ml of concentrated HCl. The resultant yellow product was collected by suction filtration, washed with water and dried at 80° C. under vacuum.

EXAMPLE B

N-(para-carboxyphenyl)nadimide was prepared as follows. Cis-5-norbornene-endo-2,3-dicarboxylic anhydride (19.14 g) was gently heated in 70 ml of acetone until it dissolved. To this solution, an equimolar amount of para-aminobenzoic acid (16.05 was added with rapid stirring. The reaction mixture turned the color white with a slight tinge of pink. Heating was stopped after five minutes and stirring maintained for about 20 minutes to ensure complete reaction. The amic acid intermediate which was then dried overnight at 65° C. under vacuum.

The dried intermediate material was then suspended in 65 ml of dimethyl formamide and heated to 45° C. Acetic anhydride (30 ml) and anhydrous sodium acetate (1.27 g) were then added with stirring. The reaction was allowed to proceed at 45° C. for two hours after which the mixture was poured into one liter of water slightly acidified by addition of 10 ml of concentrated HCl. The resultant white product was collected by suction filtration, washed with water and dried at 80° C. under vacuum.

EXAMPLE C

N-(para-carboxyphenyl)methyl nadimide was prepared as follows. Methyl-5-norbornene-2,3-dicarboxylic anhydride (18.48 g) was dissolved in 45 ml of acetone. To this solution, an equimolar amount of para-aminobenzoic acid (14.2 g) was added with rapid stirring. The reaction mixture turned the color yellow. Stirring was maintained for about 20 minutes to ensure complete reaction. The yellow intermediate material was then dried overnight at 65° C. under vacuum.

A cyclodehydration reaction was then performed on the dried intermediate material in the manner of Examples A and B. The resultant white product was collected by suction filtration, washed with water and dried at 80° C. under vacuum.

EXAMPLE D

Para-maleimidobenzoyl chloride was prepared in accordance with the procedure described by Adams et al. in J. Am. Chem. Soc., 42, 599 (1920). The N-(para-carboxyphenyl) maleimide (15 g) was suspended in about 80 ml of benzene with stirring. To this mixture was added 15 ml (a 2.5:1 molar excess) of oxalyl chloride, whereupon some gas was evolved. The mixture was then heated slowly to reflux and maintained at reflux for two hours. Excess oxalyl chloride was removed by distillation. The reaction mixture was then cooled and the yellow product recovered by suction filtration. The resultant product was washed with hexane and dried under vacuum at room temperature.

EXAMPLE E

Para-nadimidobenzoyl chloride and para-(methyl nadimido)benzoyl chloride were prepared from the products of Examples B and C in the same manner as Example D.

EXAMPLE F

Preparation of 2,2'-bis(trifluoromethyl)-4,4'-aminobiphenyl was carried out as follows. Into a 1000 ml flask equipped with a condenser and an overhead mechanical stirrer was placed a solution of 200 g of 2-bromo-5-nitrobenzotrifluoride in 350 ml dimethyl formamide. To this solution was added with stirring, purified copper powder. The mixture was stirred well at reflux for six hours and allowed to cool slowly to room temperature. The mixture was filtered to separate copper residue and the filtrate was poured into water to precipitate an intermediate product of 2,2'-bis(trifluoromethyl)-4,4'-nitrobiphenyl. This intermediate product was collected by suction filtration and dried under vacuum at 50° C. for three days.

The intermediate product (17.11 g) was placed into a round bottom flask with 135-140 ml hot 95% ethanol. To this mixture was added with stirring 72 g of stannous chloride dihydrate. Concentrated hydrochloric acid (108 ml) was then carefully added with some evolution of gas. The admixture was refluxed for 18 hours. Ethanol was subsequently removed and water added to the remaining mixture. The pH of the mixture was adjusted to neutral with 20% aqueous sodium hydroxide. The resultant product was collected by suction filtration and dried at 65° C. under vacuum overnight. The product was recrystallized from chloroform/hexane to yield tan crystals having a melting point of 182° C.

EXAMPLE 1

Preparation of 2,2'-dimethylbiphenyl bismaleimide amide monomer, shown in FIG. 1(a), was as follows. 2,2'-dimethyl-4,4'diamino-1,1'-biphenyl dihydrochloride, 6.14 g, (as described by Pickett et al. in J. Am. Chem. Soc., 72, 44-48 (1950)) was dissolved in 60 ml chloroform with 12 ml of triethylamine. The solution was cooled in an ice bath and 10 g of the acid chloride from Example D dissolved in 60 ml chloroform was carefully added with stirring. Stirring was continued for about 30 minutes to ensure complete reaction. The resultant product was collected by suction filtration, recrystallized from nitrobenzene and dried at 80° C. under vacuum. The 2,2'-dimethylbiphenyl bismaleimide monomer had a sharp endotherm at 342° C. followed by a sharp exotherm at 345° C. as determined from differential scanning calorimetry.

EXAMPLE 2

Preparation of 2,2'-dimethylbiphenyl bisnadimide amide monomer, shown in FIG. 1(b), was as follows. The diamine dihydrochloride as in Example 1 (1.92 g or 0.0067 mole) was dissolved in 20 ml chloroform with 3.7 ml of triethylamine. The solution was cooled in an ice bath and 0.0133 moles of the para-nadimidobenzoyl chloride from Example E was carefully added with stirring. Stirring was continued for about 30 minutes to ensure complete reaction. The resultant product was collected by suction filtration, recrystallized from dimethyl formamide/acetonitrile and dried at 80° C. under vacuum. The 2,2'-dimethylbiphenyl bisnadimide monomer had two broad endotherms at 292° C. and 333° C., followed by an exotherm attributed to polymerization as determined from differential scanning calorimetry.

EXAMPLE 3

Preparation of 2,2'-dimethylbiphenyl bis(methyl nadimide) amide monomer, shown in FIG. 1(c), was as follows. The diamine dihydrochloride as in Example 1 (0.69 g, 0.00238 moles) was dissolved in 10 ml chloroform with 1.3 ml of triethylamine. The solution was cooled in an ice bath and 1.5 g (0.00475 moles) of the para-(methyl nadimido)benzoyl chloride from Example E was carefully added with stirring. The reaction was exothermic. Stirring was continued for about 30 minutes to ensure complete reaction. The resultant product was collected by suction filtration, recrystallized from dimethyl formamide/water and dried at 80° C. under vacuum.

EXAMPLE 4

Preparation of 2,2'-bis(trifluoromethyl)biphenyl bismaleimide amide monomer, shown in FIG. 1(d), was as follows. The diamine from Example F was dissolved (1.0 g, 0.00312 moles) in 10 ml of chloroform with 0.87 ml of triethylamine. The solution was cooled in an ice bath and 1.472 g of the acid chloride from Example D was carefully added with stirring. Stirring was continued for about 30 minutes to ensure complete reaction. The resultant product was collected by suction filtration, recrystallized from dimethyl formamide/acetonitrile and dried at 80° C. under vacuum.

EXAMPLE 5

Preparation of 2,2'-bis(trifluoromethyl)biphenyl bisnadimide amide monomer, shown in FIG. 1(e), was as follows. The diamine from Example F (1.0 g, 0.00312 moles) was dissolved in 10 ml chloroform with 0.87 ml of triethylamine. The solution was cooled in an ice bath and 1.886 g of the para-nadimidobenzoyl chloride from Example E was carefully added with stirring. The reaction was exothermic. Stirring was continued for about 30 minutes to ensure complete reaction. The resultant product was collected by suction filtration, recrystallized from dimethyl formamide/water and dried at 80° C. under vacuum. The 2,2'-bis(trifluoromethyl)biphenyl bisnadimide monomer had two broad endotherms at 275° C. and 310° C., followed by an exotherm attributed to polymerization as determined from differential scanning calorimetry.

EXAMPLE 6

Preparation of 2,2'-bis(trifluoromethyl)biphenyl bis(methyl nadimide) amide monomer, shown in FIG. 1(f), was as follows. The diamine from Example F (1 0 g, 0.00312 moles) was dissolved in 10 ml chloroform with 0.87 ml of triethylamine. The solution was cooled in an ice bath and 1.974 g of the para-(methyl nadimido)benzoyl chloride from Example E was carefully added with stirring. The reaction was exothermic. Stirring was continued for about 30 minutes to ensure complete reaction. The resultant product was collected by suction filtration, recrystallized from of methanol/water and dried at 80° C. under vacuum.

While the present invention has been described with reference to specific details, it is not intended that such details should be regarded as limitations upon the scope of the invention, except as and to the extent that they are included in the accompanying claims.

What is claimed is:

1. A thermoset polyamide composition comprised of cured segments derived from one or more polyamide monomers represented by the formula: $R^1-A^1-B^1-A^2-B^2-A^3-R^2$ where $R^1$ and $R^2$ are the same radical selected from the group consisting of maleimide, nadimide, methyl nadimide, ethynyl, and $(C(R^3)_2)_2$ where $R^3$ is hydrogen with the proviso that the two carbon atoms of $(C(R_3)_2)_2$ are bound on the aromatic ring of $A^1$ or $A^3$ to adjacent carbon atoms, $A^1$ and $A^3$ are selected from the group consisting of 1,4-phenylene and the same where said groups contain one or more substituents selected from the group consisting of halo, nitro, lower alkyl, lower alkoxy, fluoroalkoxy or fluoroalkyl, $A^2$ is selected from the group consisting of 1,4-phenylene, 4,4'-biphenyl, 2,6-naphthylene and the same where said groups contain one or more substituents selected from the group consisting of halo, nitro, lower alkyl, lower alkoxy, fluoroalkoxy or fluoroalkyl, and $B^1$ and $B^2$ are selected from the group consisting of —C(O)—N(H)— and —N(H)—C(O)—, wherein at least one of the polyamide monomers is characterized as liquid crystalline.

2. The thermoset polyamide composition of claim 1 wherein in at least one monomer $R^1$ and $R^2$ are nadimide groups, $A^1$ and $A^3$ are 1,4-phenylene, $A^2$ is a 4,4'-biphenyl group containing a methyl substituent upon each ring, and $B^1$ and $B^2$ are —C(O)—N(H)— groups wherein the —C(O)— functionalities of $B^1$ and $B^2$ are adjacent to $A^1$ and $A^3$, wherein said curable polyamide monomer is characterized as liquid crystalline.

3. The thermoset polyamide composition of claim 1 wherein in at least one monomer $R^1$ and $R^2$ are methyl nadimide groups, $A^1$ and $A^3$ are 1,4-phenylene, $A^2$ is a 4,4'-biphenyl group containing a methyl substituent upon each ring, and $B^1$ and $B^2$ are —C(O)—N(H)— groups wherein the —C(O)— functionalities of $B^1$ and $B^2$ are adjacent to $A^1$ and $A^3$, wherein said curable polyamide monomer is characterized as liquid crystalline.

4. The thermoset polyamide composition of claim 1 wherein in at least one monomer $R^1$ and $R^2$ are methyl nadimide groups, $A^1$ and $A^3$ are 1,4-phenylene, $A^2$ is a 4,4'-biphenyl group containing a trifluoromethyl substituent upon each ring, and $B^1$ and $B^2$ are —C(O)—N(H)— groups wherein the —C(O)— functionalities of $B^1$ and $B^2$ are adjacent to $A^1$ and $A^3$, wherein said curable polyamide monomer is characterized as liquid crystalline.

5. A curable blend comprised of at least two polyamide monomers represented by the formula: $R^1-A^1-B^1-A^2-B^2-A^3-R^2$ where $R^1$ and $R^2$ are radicals selected from the group consisting of maleimide, substituted maleimide, nadimide, substituted nadimide, ethynyl, and $(C(R^3)_2)_2$ where $R^3$ is hydrogen with the proviso that the two carbon atoms of $(C(R^3)_2)_2$ are bound on the aromatic ring of $A^1$ and $R^3$ to adjacent carbon atoms, $A^1$ and $A^3$ are 1,4-phenylene and the same where said group consisting of halo, nitro, lower alkyl, lower alkoxy, fluoroalkoxy or fluoroalkyl, $A^2$ is selected from the group consisting of 1,4-phenylene, 4,4'-biphenyl, 2,6-naphthylene and the same where said groups contain one or more substituents selected from the group consisting of halo, nitro, lower alkyl, lower alkoxy, fluoroalkoxy or fluoroalkyl, and $B^1$ and $B^2$ are selected from the group consisting of —C(O)—O— and —O—C(O)—, with the proviso that at least one of the polyamide monomers is characterized as liquid crystalline.

6. A process of preparing a curable polyamide monomer represented by the formula: $R^1-A^1-B^1-A^2-B^2-A^3-R^2$ where $R^1$ and $R^2$ are the same radical selected from the group consisting of nadimide, and methyl nadimide, $A^1$ and $A^3$ are 1,4-phenylene, $A^2$ is 4,4'-biphenyl and the same where said group contains one or more substituents selected from the group consisting of methyl and trifluoromethyl, and $B^1$ and $B^2$ are selected from the group consisting of —C(O)—N(H)— and —N(H)—C(O)—, said curable polyamide monomer characterized as liquid crystalline, said process comprising: reacting a difunctional compound represented by the formula $B^3-R^4-B^4$ wherein $B^3$ and $B^4$ are selected from the group consisting of —NH$_2$ or —NH$_2$.HCl, and $A^2$ is 4,4'-biphenyl and the same where said group contains one or more substituents selected from the group consisting of methyl and trifluoromethyl, with an acid chloride represented by the formula: $Cl-C(O)-A^1-R^1$ where $A^1$ is 1,4-phenylene, and $R^1$ is a radical selected from the group consisting of nadimide, and methyl nadimide, to yield a curable polyamide monomer characterized as liquid crystalline.

* * * * *